(12) United States Patent
Silverman

(10) Patent No.: US 6,221,611 B1
(45) Date of Patent: Apr. 24, 2001

(54) USE OF ABP AS A PROGNOSTIC AND DIAGNOSTIC INDICATOR

(75) Inventor: Robert Silverman, New Hyde Park, NY (US)

(73) Assignee: Signet Laboratories, Inc., MA (US)

( * ) Notice: Subject to any disclaimer, the term of this patent is extended or adjusted under 35 U.S.C. 154(b) by 0 days.

(21) Appl. No.: 09/065,286

(22) Filed: Apr. 23, 1998

Related U.S. Application Data

(63) Continuation of application No. 08/656,584, filed on May 31, 1996, now abandoned.
(51) Int. Cl.[7] .................. G01N 33/53; G01N 33/537; G01N 33/566; G01N 33/543
(52) U.S. Cl. .................. 435/7.1; 435/7.92; 436/501; 436/518; 436/548
(58) Field of Search .......................... 435/7, 240.1, 7.1, 435/7.92; 436/548, 520, 501, 518

(56) References Cited

U.S. PATENT DOCUMENTS 4,731,326 * 3/1988 Thompson et al. .

OTHER PUBLICATIONS

Westhuyzen et al (Clinica Chimica Acta vol. 228 pp 123–132, 1994.*
Tolkoff—Rubin et al. Nephro. Dial. Transplant 2:143–148, 1987.*
Thompson et al. Clin. Chem 31(5):679–683, 1985.*
Cerra et al. Arch. Surg. 125:519–522, 1990.*
Lemeshow et al. JAMA 270(20):2478–2485, 1993.*

* cited by examiner

*Primary Examiner*—Albert Navarro
(74) *Attorney, Agent, or Firm*—Fulbright & Jaworski, LLP

(57) ABSTRACT

This invention relates to the use of urine ABP measurement in the diagnosis of serious systemic infection, and in the determination of increased chance of mortality.

5 Claims, No Drawings

USE OF ABP AS A PROGNOSTIC AND DIAGNOSTIC INDICATOR

RELATED APPLICATION

This application is a continuation of Application Serial No. 08/656,584, filed May 31, 1996, now abandoned.

FIELD OF THE INVENTION

This invention relates to the use of ABP as a prognostic and diagnostic indicator. Specifically, the level of ABP in the urine is measured. An increased level of AEP measured on hospital arrival indicates the presence of serious systemic infection, and also indicates an increased chance of mortality during hospitalization. ABP measurement in the urine can be used either alone or in conjunction with other known tests to determine mortality.

BACKGROUND OF THE INVENTION

Adenosine deaminase binding protein (referred to herein as "ABP") is a 120,000 dalton surface glycoprotein found on the brush border of the kidney proximal tubular epithelial cell. In addition to the proximal tubule, ABP has been detected in human prostate tissue, skin, renal medulla and mucosa of the intestinal tract. Smaller amounts have been detected in the liver, lung, pancreas and endometrial tissue.

ABP is released in the urine when the proximal tubule of the kidney is affected. ABP has therefore been used as a marker for acute renal injury (Thompson et al., Toxicol. Pathol., Vol. 14, p. 232–237 (1986)). For example, ABP is released in high concentrations in the urine in patients with acute renal tubular necrosis (Goren, et al., Am J. Clin. Pathol., Vol. 86, p. 780–783 (1986)). In addition, patients with renal transplant rejection have high concentrations of ABP in the urine (Tolkoff-Rubin, et al., Transplantation, Vol. 41, p. 593–597 (1986)). High levels of ABP are not found in patients with glomerular disease, prerenal azotemia, or in healthy controls (Tolkoff-Rubin, Kidney International, Vol. 29, p. 142–152 (1986)).

Other proteins have been used as indicators of renal disease. These include N-acetyl-$\beta$-D-glucosaminidase, b2-microglobulin and microsomal aminopeptidase (see Vanderlinde, Ann. Clin. Lab. Sci., Vol. 11, 189–201 (1981) and Price, Toxicoloy, Vol. 23, p. 99–134 (1982)). However, clinical use of these markers is limited as they are not disease- or condition- specific. Further, these proteins are unstable in urine, and are subject to enzyme inhibitors and other interfering substances in the urine.

The inventor of the instant application has determined that high levels of ABP in the urine can be used as a prognostic indicator for mortality and as a diagnostic indicator for sepsis, or serious systemic infection. ABP is measured in the urine utilizing an ELISA technique. It has been determined that ABP concentrations are elevated with several acute medical illnesses. These include illnesses caused by infectious diseases, usually caused by bacteria. In addition, patients with high levels of ABP in the urine have increased mortality as compared with individuals having normal ABP levels in the urine. Hence, ABP urine measure is a marker for serious systemic infection and for certain types of acute illness, and is also a marker for increased mortality.

Prior here to, clinicians have relied on certain symptoms, signs and objective measures to determine severity of illness. For example, clinicians have used an altered mental status, decreased urine output, high pulse rate, high respiratory rate and/or decreased blood pressure to indicate the presence of a systemic process that is significantly effecting a patient's health. However, these variables only reflect biochemical changes that occur in the body. If one can detect the substances that are released in response to insult to the body, which substances are found before the physiological abnormalities described, then one can treat the causative disease at earlier stages, as once an infection leads to sepsis, mortality rates range from 50–75%. Also, it may be difficult to distinguish a relatively benign condition from a more serious illness at the earliest stages, as clinically they may appear to be similar. The marker described herein, ABP, can be used as part of the clinicians judgment, alone or in conjunction with other objective tests and severity of illness scales, to identify patients with more significant illness.

SUMMARY OF THE INVENTION

This invention is directed to a method of diagnosing serious systemic infection. Such infections include, but are not limited to, pneumonia, cellulitis, gastroenteritis, pyelonephritis and joint infection. Serious systemic infection is diagnosed in a subject by measuring the level of ABP in the urine of said subject. An increased ABP level indicates an increased likelihood of a positive diagnosis.

This invention is further directed to a method of determining an increased chance of mortality in a subject. The level of ABP in the urine of a subject is measured. An increased level of ABP in the urine indicates an increased chance of mortality. This test can be combined with other known tests, such as APACHE II, SAPS II or MPM, to determine an increased chance of mortality in a subject.

DETAILED DESCRIPTION OF THE INVENTION

In the studies described herein, in order to measure ABP in the urine, urine was collected and refrigerated until assayed. It was determined that storage of urine for as long as 6–12 months did not affect the accuracy of the ABP measurement test. For all of the data collected, urine samples were batched and analyzed, in most cases in a matter of days after the patient was evaluated.

The presence and level of ABP in the urine was determined by ELISA using the monoclonal antibodies designated S23 and S27 and the ELISA technique described in U.S. Pat. No. 4,731,326, the entirety of which is incorporated herein by reference. To verify accuracy, several of the same samples were assayed more than two times.

The sensitivity of the test was set at 0.05 units of reactivity. Concentrations of ABP below this level could not be accurately determined by the assay. The results are given in units of reactivity, defined as the amount of ABP present in a 100 $\mu$l sample that increases absorbance at 490 nm by one absorbance unit in the assay. The minimum ABP level which indicates serious systemic illness or impending mortality is 0.2 units.

Example 1

Normal (control) ranges of ABP in urine were first determined. To do this, random urine samples from healthy individuals were tested. Urine concentrations of ABP in controls were found to be less than 0.10 units in all cases, and less than 0.05 units in almost all cases. The healthy individuals tested (n=20) were less than 50 years old.

Another set of individuals (n=23) over the age of 50, with a variety of chronic illness, including controlled diabetes, coronary heart disease and hypertension, were also tested.

All of these individuals were found to have ABP levels of less than 0.05 units in the urine. Further, young adults with acute exacerbations of asthma (n=12) were tested, and found to have ABP levels of less than 0.05 units in the urine. In addition, individuals with renal colic (n=16) were tested for ABP levels. 14 out of 16 individuals had levels of less than 0.05 units and the other 2 had levels of less than 0.10 units. These results indicate that the aforementioned conditions do not cause an increase of ABP level in the urine.

Example 2

Patients with urinary tract infections who were admitted to the emergency room were tested for urine ABP levels. It is important to distinguish a bladder infection (cystitis) from a kidney infection (pyelonephritis). Bladder infections, although uncomfortable, are usually benign and self-limited. In contrast, untreated kidney infections can result in permanent organ damage or can spread throughout the body. Kidney infections are therefore treated more aggressively and observed more carefully than bladder infections. Urine ABP levels were tested for both of these conditions.

The first subgroup tested included patients with uncomplicated bladder infections. This was clinically defined as the presence of acute urinary discomfort, lack of fever, no need for hospitalization, no other acute medical problems, no CVA tenderness, and the presence of bacteria and white blood cells in the urine. 18 patients were in this group. 16 patients were found to have urine ABP levels of less than 0.05 units. 2 patients were found to have urine ABP levels of 0.07.

In a second subgroup, 14 patients with pyelonephritis (kidney infection) were identified. Pyelonephritis was defined by the presence of fever, white blood cells in the urine, and either gastrointestinal symptoms or CVA tenderness without other apparent acute extrarenal medical problems. 7 of the 14 patients in this group were found to have ABP levels of less than 0.05 units, and 7 of the 14 patients were found to have levels ranging from 0.07–0.72 units (mean=0.33 units). No ADP levels greater than 0.10 units were found in patients with bladder infections. Therefore, a positive test result could indicate the presence of a kidney infection. However, the absence of high urine ABP levels does not necessarily indicate the absence of kidney infection, since half of the patients with kidney infection did not have increased ABP levels.

It is possible that negative ABP values were obtained for some patients in the kidney infection group because the proximal tubules of the kidneys were not involved in the infections. It is known that focal, rather than diffuse, areas of infection are common in patients with pyelonephritis. It is also possible that the elevations were related to systemic response, rather than localized infiltration of the proximal tubules. The presence of pyuria (white cells in the urine) did not cause an elevation of ABP in these studies.

Example 3

A selected sample of extremely ill patients admitted to the emergency room with fever (febrile patients) were tested for ABP levels in the urine. Baseline urine samples were obtained in the emergency room and prior to the patient receiving antibiotics, and urine was stored for future ABP analysis. A medical history and evaluation was recorded for each patient. Outcome of hospitalized patients were also recorded. APACHE II scores, as discussed below, were calculated based on data available in the emergency room.

The average age of these patients was 58 years, ranging from 19–93. 80% of patients were admitted to the hospital, consistent with the selection of the most ill patients on emergency room arrival. 28% of admitted patients expired in the hospital. APACHE II tests were performed. APACHE II is a weighted prognostic index which predicts mortality. It identifies a number of clinical or lab findings, and assigns points to each. The more abnormal the clinical variable, the more points given. Although the APACHE II test is typically used to predict mortality in intensive care patients, it was used to evaluate this population since there are currently no tests designed specifically for evaluating acutely ill emergency room patients. The median APACHE II score was 11 in all patients.

18 of these febrile patients were discharged from the emergency room. All of these 18 febrile patients were found to have negative ELISA (no increased ABP levels in the urine). 72 patients were admitted to the hospital. 15 of these patients expired within 30 days of being admitted to the hospital. Of the 15 patients who expired within 30 days of hospitalization, 13 (89%) had positive ABP ELISA results (at least 0.2 units) upon arrival at the emergency room. 20 of the 54 patients (37%) who were admitted to the hospital and survived to discharge had a positive ELISA. Two out of 38 (5%) of patients with a negative ABP ELISA (less than 0.2 units) expired in hospital and within 30 days of admission, compared to 13 out of 31 (42%) patients with a positive ELISA. Several variables were collected while the patients were still in the emergency room. These variables were found to correlate significantly with death ($p<0.05$): temperature, altered mental status, age, APACHE II score, clinicians assessment and ABP ELISA positivity. Clinicians assessment of likelihood of in-house mortality was categorized as either 'unlikely' or 'possible'.

Using a regression analysis, both the ABP ELISA and clinician's assessment were found to be the strongest predictors of in hospital mortality. In a post hoc tabulation, these two variables were combined to predict mortality (n=47) (not all data available on all patients for the regression analysis):

| CATEGORIES | MORTALITY |
| --- | --- |
| Death unlikely, ELISA negative | 0/14 |
| Death unlikely, ELISA positive | 2/8 (25%) |
| Death possible, ELISA negative | 4/12 (33%) |
| Death possible, ELISA positive | 11/13 (84%) |

When clinical judgement was not used in the regression analysis, ELISA and APACHE II were the most important mortality indicators. The APACHE II score was calculated by adding the variables that were obtainable in the emergency room. For the purpose of analysis, an APACHE II score of 15 or above was considered a strong predictor of death. Again, in a post-hoc analysis, these two variables were combined to predict in-hospital death (n=66):

| CATEGORY | MORTALITY |
| --- | --- |
| APACHE <14, ELISA negative | 0/25 |
| APACHE <14, ELISA positive | 5/15 (33%) |
| APACHE >15, ELISA negative | 5/11 (46%) |
| APACHE >15, ELISA positive | 9/15 (60%) |

Hence, a single increased ABP urine measurement obtained on arrival to the emergency room was a strong predictor of in-hospital death. When combined with clinical judgement or an APACHE score, the ABP result enhanced the ability to predict death or survival.

Example 4

In a second study, 441 patients over the age of 18 presenting to the emergency room with medical illnesses were evaluated. Patients were included regardless of initial body temperature. Patients were recruited from the acute medical division of the emergency room, which means that trauma patients and those with minor complaints were excluded. Urine was obtained at the earliest possible time in the emergency room, and historical and clinical variables were recorded. The population chosen for this part of the experiment represents unselected patients, who were therefore less ill than those identified in the previous example.

The median age of patients tested was 64 years. 95 out of the 441 patients (22%) had a positive ELISA. 84 out of 354 admitted patients (24%) had a positive ELISA, and 11 out of 87 discharged patients (13%) had a positive ELISA. 33% of all febrile patients (temperature >100.2) had a positive ELISA and 14% of all afebrile patients had a positive ELISA.

The median age of patients discharged from the emergency room was younger than hospitalized patients (42 vs 67 years). 11 of the 87 discharged patients had a positive ABP ELISA. 8 of the 11 positives were relatively low, ranging from 0.2–0.35 units.

10 of the 11 patients discharged with positive urine ABP levels were diagnosed with infectious illnesses. Diagnoses included cellulitis, pharyngitis, pneumonia, gastroenteritis, pyelonephritis and skin abscess. One patient had a noninfectious illness. This patent had borderline positive results, which were negative when retested. All patients with positive ABP results were presumed to have a bacterial organism causing the illness, since they were discharged on antibiotics or required a procedure to drain purulent material.

The overall death rate in admitted patients was 22 out of 354 (6.26%). Seven patients were excluded from further analysis, since tests would not serve any purpose. The seven patients included: three patients receiving cardiopulmonary resuscitation either on or soon after hospital arrival, and never regained spontaneous pulse or respiration; three patients who died after 30 inpatient days; and one patient who had a "do not resuscitate" order on emergency room arrival and expired in the emergency room.

The following data reflects the other 15 patients who died in hospital:

| Overall mortality | |
| --- | --- |
| positive ELISA | 7/83 (8%) |
| negative ELISA | 8/255 (3%) |
| Mortality in admitted febrile patients | |
| positive ELISA | 4/47 (9%) |
| negative ELISA | 2/75 (3%) |
| Mortality in afebrile admitted | |
| positive ELISA | 1/34 (3%) |
| negative ELISA | 6/180 (3%) |

Of the 6 febrile patients who died in hospital, 4 had a positive urine ABP. Of the 2 who died with a negative urine ABP, the exact cause of death was never established. The 2 patients with negative ELISAs had levels of 0.06 and 0.13 units (intermediate or equivocal).

Of the 7 afebrile patients who died in hospital, 1 had a positive ELISA. This patient had the admitting diagnosis of a UGI bleed. Two other patients who died did not have a temperature recorded on hospital arrival. Both had a positive ELISA.

Final discharge diagnoses were obtained from the medical records of the patents. It was determined that certain specific infectious or inflammatory illnesses were more likely to coincide with positive ELISA values. The following illness categories, and ABP results, include some patients who were not hospitalized:

| Patients with Pneumonia | |
| --- | --- |
| positive ABP | 15/31 (48%) |
| equivocal ABP | 6/31 (19%) |
| negative ABP | 10/31 (32%) |
| Patients with cellulitis | |
| positive | 7/11 (64%) |
| equivocal | 2/11 (18%) |
| negative | 2/11 (18%) |
| Patients with joint inflammation | |
| positive | 4/4 (100%) |
| equivocal | 0/4 |
| negative | 0/4 |
| Patients with gastroenteritis | |
| positive | 3/9 (33%) |
| equivocal | 1/9 (11%) |
| negative | 5/9 (565) |

Five patients who had the clinical diagnosis of sepsis made in the emergency room, and subsequently died in hospital, were identified. All of these patients had temperature over 100.2°, pulse over 90 and initial respiratory rates over 20. The ABP levels were 0.13, 0.31, 0.63, 0.68 and 1.49 for these patients.

Example 5

The Mortality Probability Model (MPM) scale (Lemeshow et al., JAMA, Vol. 270, p. 2478 (1993)) was used in place of the APACHE II test to predict illness outcome, since MPM depends on variables which are more likely to be obtained in the emergency room. When ABP results were placed in a stepwise regression as a continuous variable, ABP added to the ability to predict death. When the results from the MPM were partialed, 6 patients were predicted in the emergency room to have mortality rates ranging from 10–80%. However, when the ABP results were assessed, the ability to predict death was enhanced in 5 out of 6 of these patients.

The data described herein shows that a single elevated urine ABP level obtained in the emergency room not only identifies patients who are acutely ill, but also assists in predicting outcome. Of the patients with a positive ELISA, all required antibiotics, a procedure to drain pus, and/or hospital admission. Therefore, a positive ELISA indicated the need for medical intervention. In addition, certain infectious diseases that are typically caused by bacterial pathogens typically correlated with positive ABP levels. A positive ELISA in febrile patients predicted a higher in-hospital mortality. Patients with a diagnosis of sepsis who died in hospital had equivocal or positive ABP levels upon emergency room arrival. None had negative levels. Hence, positive ABP levels can be used to predict mortality. The ABP test of the present invention can also be used in conjunction with Simplified Acute Physiology Score (SAPS II) (LaGall et al., JAMA, Vol. 270, p. 2957–2963 (1993)).

Urine levels appear to be elevated (greater than 0.20 units) in conditions associated with systemic inflammatory, ischemic or toxic events, independent of any clinically apparent renal involvement. Conditions which are associated with elevated urine ABP levels include pneumonia, cellulitis, gastrointestinal infections, joint infections, and pleural effusions. Other conditions are occasionally associated with elevated urine ABP levels when all febrile patients are included. These conditions include myocardial infarction, unstable angina, hemorrhagic CVA, upper GI bleed, Sickle cell crisis, arrhythmias, bacteremia without source, bacteremia with gall bladder infection and pyelonephritis. Still other conditions are associated with low (normal) urine ABP levels. These include asthma, minor trauma, bladder infections, systemic viral infections, localized viral infections, dehydration, fever from environmental sources (heat related illness),severe pain associated with renal colic and musculoskeletal pain.

Measurement of ABP in the urine can be used to identify high risk patients. A single increased urine level obtained in the emergency room serves as a marker for illness, and indicates that medical intervention is required. Patients with high urine ABP levels need hospital admission, or require treatment for a bacterial infection. The test may be used when the diagnosis is unclear (bacterial versus viral illness for example), or when it is uncertain if the patient requires hospitalization. A positive test can therefore supplement the clinicians judgement. Increased ABP levels also add prognostic accuracy to established severity of illness scores. ABP measurement can be used as an additional variable on an established scale (e.g. APACHE II and/or MPM).

As discussed hereinabove, measurement of ABP in the urine can also be used as an indicator for in hospital mortality. Acutely ill febrile patients admitted with high ABP levels are 3 times more likely to die than febrile patients with low levels when all febrile patients are included, and 8 times more likely to die when severely ill patients are identified. Additional monitoring or testing, or consideration for more aggressive treatment, may be considered when patients are found to have increased ABP levels.

ABP measurement can also be used to identify patients with serious systemic illness who are more likely to die. The data described herein indicates that admitted patients who die from serious systemic illness have abnormal ABP levels in the emergency room. Positive ABP results indicate intensive patient care is required to treat sepsis. Negative ABP levels can identify patients who are least likely to benefit from costly, and possibly dangerous, anti-sepsis therapy.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

I claim:

1. A method for detecting presence of an infectious illness requiring treatment or hospitalization of a subject, said infectious illness selected from the group consisting of pneumonia, cellulitis, gastroenteritis and joint infection, comprising measuring the level of adenosine binding protein in a urine sample taken from said subject, wherein a level of adenosine binding protein above 0.2 units is indicative of presence of said infectious illness in said subject.

2. A method for determining increased chance of mortality in a patient who has been diagnosed with a bacterial infection and a condition selected from the group consisting of pneumonia, pharyngitis, cellulitis, gastroenteritis, skin abscesses, and joint infection, comprising determining the level of adenosine binding protein in a urine sample taken from said patient, wherein a level of at least 0.2 units of said adenosine binding protein in said urine is indicative of an increased chance of mortality for said patient.

3. The method of claim 2, further comprising measuring said adenosine binding protein via ELISA.

4. The method of claim 2, further comprising determining an APACHE II score for said patient, a APACHE II score of 1.5 or above being further evidence of increased chance of mortality.

5. The method of claim 2, wherein said patient is febrile.

* * * * *

UNITED STATES PATENT AND TRADEMARK OFFICE
CERTIFICATE OF CORRECTION

PATENT NO. : 6,221,611 B1
DATED : April 24, 2001
INVENTOR(S) : Silverman

Page 1 of 1

It is certified that error appears in the above-identified patent and that said Letters Patent is hereby corrected as shown below:

Column 1,
Line 12, change "AEP" to -- ABP --.

Column 5,
Line 39, change "6.26" to -- 6.2 --.

Column 8,
Line 18, after "detecting" insert -- possible --.
Line 24, after "of" insert -- possible --.
Lines 33-35, after "units" delete phrase until the end of the sentence.
Line 39, change "1.5" to -- 15 --.

Signed and Sealed this

Eighteenth Day of December, 2001

Attest:

*Attesting Officer*

JAMES E. ROGAN
*Director of the United States Patent and Trademark Office*